United States Patent [19]

French et al.

[11] Patent Number: 5,131,387
[45] Date of Patent: Jul. 21, 1992

[54] MOISTURE TRAP

[75] Inventors: Gerald H. French, Overland; James E. Graham, High Ridge; Angelus M. Lombardo, Fenton, all of Mo.

[73] Assignee: Marquette Gas Analysis Corp., St. Louis, Mo.

[21] Appl. No.: 521,150

[22] Filed: May 9, 1990

[51] Int. Cl.⁵ ................. A62B 7/10; A62B 23/02
[52] U.S. Cl. ................. 128/205.27; 128/205.12; 55/316; 55/387
[58] Field of Search .............. 128/205.12, 205.27; 55/316, 323, 387, 482; 73/200

[56] References Cited

U.S. PATENT DOCUMENTS

| 2,326,925 | 8/1943 | Bortini | 128/2.08 |
| 2,528,539 | 11/1950 | Norgren et al. | 183/34 |
| 2,702,089 | 2/1955 | Engelder | 183/4.8 |
| 2,823,693 | 2/1958 | Balter | 137/197 |
| 2,823,694 | 2/1958 | Champion | 137/197 |
| 3,000,191 | 9/1961 | Stark | 62/259 |
| 3,300,949 | 1/1967 | Smylie et al. | 55/35 |
| 3,303,634 | 2/1967 | Berrian | 55/35 |
| 3,421,534 | 1/1969 | Henderson | 137/199 |
| 4,197,858 | 4/1980 | Osborn | 128/718 |
| 4,232,667 | 11/1980 | Chalon et al. | 128/203.26 |
| 4,278,453 | 7/1981 | Klein | 55/275 |
| 4,446,869 | 5/1984 | Knodle | 128/716 |
| 4,457,305 | 7/1984 | Shanks et al. | 128/205.12 |
| 4,546,778 | 10/1985 | Sullivan | 128/718 |
| 4,558,696 | 12/1985 | Eiserman | 128/205.12 |
| 4,558,708 | 12/1985 | Labuda | 128/719 |
| 4,579,568 | 4/1986 | Riccirdelli et al. | 155/189 |
| 4,713,095 | 12/1987 | Riccirdelli | 55/189 |
| 4,786,289 | 11/1988 | Billiet et al. | 55/269 |
| 4,790,327 | 12/1988 | Despotis | 128/719 |

FOREIGN PATENT DOCUMENTS 396360  11/1933  United Kingdom ........... 128/140

Primary Examiner—Kyle L. Howell
Assistant Examiner—Scott R. Akers
Attorney, Agent, or Firm—Michael, Best & Friedrich

[57] ABSTRACT

A moisture trap for use in a patient monitoring system, includes hydrophilic material contained within a housing for separating moisture from the patient's exhalations prior to those exhalations reaching the actual monitoring device. The housing is separated into a reservoir containing hydrophilic medium and a passageway through which the exhalations flow. The reservoir is isolated from the passage except for a restricted passage, that restricted passage providing the only exposure of reservoir hydrophilic material to moisture and gaseous medium flowing through the passageway. A hydrophilic body is also positioned in the passageway in the path of exhalation flow. A wick of hydrophilic material in the restricted opening connects the passageway and hydrophilic body in the passageway to the hydrophilic reservoir material. A hydrophobic member is positioned in the flow path of the exhalations to occlude and interrupt the flow path when the hydrophilic material becomes saturated and can no longer pick up moisture.

27 Claims, 1 Drawing Sheet

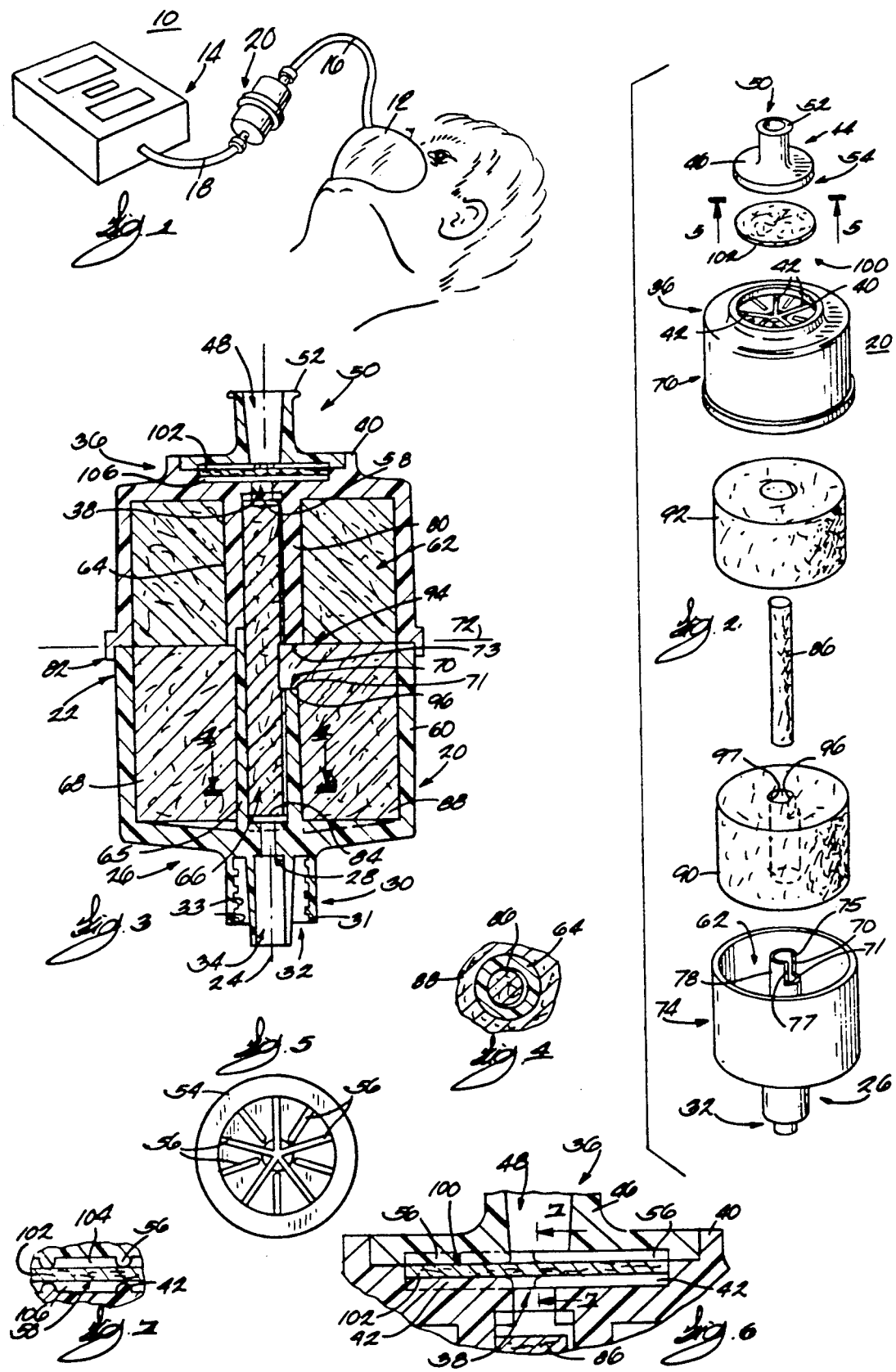

MOISTURE TRAP

BACKGROUND OF THE INVENTION

The invention relates generally to systems for monitoring a medical patient's condition, and more particularly to monitoring systems including a moisture trap for removing moisture which has condensed from a patient's exhalation.

In the course of medical treatment, it is often desirable to monitor a patient's exhalation and, in some instances, analyze its gaseous composition. This may be monitoring, for instance, for apnea or analyzing the exhalation of a patient under anesthesia. Typically, the patient's exhalation is monitored by transferring a portion of the patient's exhalation to a suitable sensor.

Accurate analysis of the gases in a patient's exhalation depends upon the collection of the flow of exhalation without the introduction of factors which might distort the results of the analysis. Introduction of contaminants into the flow, or other alteration of the exhalation in the monitoring system, can render analytical results which do not reflect the actual condition of the patient.

Because a patient's exhalation is usually relatively humid, moisture must be removed before the sensor. Moreover, water can condense as the exhalation flows from the patient to the sensor. This then identifies two possible sources of moisture contamination, i.e., entrainment in the exhalation per se and re-entrainment of prior condensation into a subsequent stream of exhalation. Condensation can result in inaccurate readings at the sensor. In addition, collected condensation can interrupt the smooth flow of exhalation to the sensor, another possible distortion of the sensor operation.

Also, sensing devices used in patient monitoring systems, such as an infrared spectrometer, are often delicate and can be uncalibrated by moisture entering the sensor.

In order to remove moisture from the exhalation to prevent distortion of the gaseous composition of the exhalation and to protect the sensing devices, it has been known to place a moisture trap between the patient and the sensing device to separate moisture from the exhalation before it enters the sensing device.

Some prior art moisture trap designs utilize a porous, hydrophilic material to separate water vapor from a flow of exhalation. While hydrophilic materials can effectively remove a quantity of condensed moisture from a flow of humid gas, their use in some prior moisture trap designs have introduced other problems. More specifically, hydrophilic materials are porous and include voids. Such prior art moisture tap designs using hydrophilic materials remove moisture from the exhalation by allowing the exhalation to pass in proximity with or through the hydrophilic material. These arrangements can alter the gaseous composition of the exhalation being monitored by allowing gases held in the porous hydrophilic material to become re-entrained with and mix with the flow of exhalation. More specifically, this could be in the form of previously exhaled air or sample gas which had been held in the voids and which is later released into a subsequent stream of exhaled air or sample gas, thereby distorting the gas content of that subsequent stream such that when the stream reaches the sensor, it is not an accurate representation of the patient's condition at that instant. The greater the volume of hydrophilic material exposed to the flow of exhalation, generally the greater volume of gas which can be stored therein and then be available to later contaminate the exhalation. Minimizing the volume of hydrophilic material used in some prior art designs can decrease the amount of such mixing, but can also undesirably decrease the capacity of the moisture trap.

It is an object of the invention to provide a moisture trap for removing condensed moisture from a flow of exhalation without altering the gaseous composition of the exhalation.

It is a further object of the invention to provide a moisture trap having an expanded capacity to absorb condensed moisture from a patient's exhalation which assures that moisture will not pass through the moisture trap and into the sensor thereby protecting the sensor.

Among the more specific objects of this invention is to provide a moisture trap which provides a smooth flow of exhalation from the patient to the sensor in a fluid flow sense, while achieving increased moisture separation and minimizing the possibility of entrainment and contaminants in a given stream of exhalation.

Yet another specific object of this invention is to effectively interrupt the flow of exhalations when the moisture trap becomes saturated and can no longer effectively separate moisture from the exhalation.

SUMMARY OF THE INVENTION

For the realization of these and other objects, this invention provides a patient monitoring system including a moisture trap located between the patient and the sensor for removing condensed moisture from the flow of exhalation prior to the sensor.

The moisture trap includes an enclosed reservoir of hydrophilic material exposed to the flow of exhalation. Moisture is separated from the stream and retained in that reservoir. The moisture trap also includes hydrophobic material positioned in the path of the flow of exhalation downstream of the hydrophilic means for occluding the moisture trap when the hydrophilic means is saturated so that exhalations can no longer pass to the sensor until the moisture trap is replaced by a fresh unit.

More particularly, the actual physical contact between the hydrophilic material and exhalations is minimized by limiting direct contact of the exhalations and the major portion of hydrophilic reservoir. In the preferred structure, the trap includes a generally central passageway which separates the trap interior into a flow passage and a larger reservoir area. The reservoir area is connected to flow passage through a restricted opening and a portion of hydrophilic material fills that opening and is exposed to the flow passage. The portion of hydrophilic material acts as a wick to transport moisture from the flow passage to the reservoir where it can be stored.

It is also preferred to include an elongated, generally cylindrical column of hydrophilic material in the flow passageway. The hydrophilic column has a cross-sectional area smaller than the cross-sectional area of the flow passage to afford a controlled, but substantially unimpeded, flow of exhalation along the central passageway. The unimpeded flow means that the pressure drop along the column is at a minimum and there is no incentive flow into or out of the column relative to the reservoir area. Exhalation will flow around the column, and to very little extent through the column, to act as an initial pick up for moisture entrained in the stream of exhalations. The columnar shape of the pick up provides an adequate surface area for a short time to remove moisture from the exhalation as the exhalation passes over the length of the column, but with a relatively small volume of hydrophilic material to minimize the volume of any gaseous medium that can become entrapped in the column and thereby minimizes the possibility of mixing contaminating gases with the later streams of exhalation.

The only communication between the passage and the hydrophilic material in the reservoir is through the wick. The wick absorbs moisture from the hydrophilic column to extend its life and to some extent directly from the exhalation stream. The wick draws moisture collected by the column away from the column, through the opening and into the reservoir. The wick becomes filled with moisture and substantially occupies the opening to effectively seal the opening to restrict passage of gas therethrough. In addition, with only one opening, there is no differential pressure between the central passage and the reservoir to cause flow. Because gases cannot readily pass between the central passageway and the reservoir, gases entrained in the exhalations cannot find their way into the reservoir and gases already in the reservoir cannot mix with and contaminate subsequent exhalation passing through the central passageway. Thus, gaseous media entrained with the exhalations pass through the trap, do not become contaminated therein by stale media, and provide a current, representative sample of the patient's exhalation at the sensor.

In order to interrupt the flow of exhalations when the moisture trap becomes saturated and can no longer effectively separate moisture from the exhalation, the moisture trap also includes means for occluding the flow passageway when excessive amounts of moisture collect in the moisture trap.

The means for occluding the passageway is located in the trap downstream of the wick and preferably downstream of the hydrophilic column. Preferably, the occluding means is in the form of a porous filter which allows passage of gases but is made of hydrophobic material to repel and prevent passage of water vapor. Water vapor repelled by the hydrophobic filter collects adjacent the hydrophobic filter and eventually occludes the filter to block passage of exhalation.

Various other features and advantages of the invention will become apparent to those skilled in the art upon review of the following detailed description, claims and drawings.

DESCRIPTION OF THE DRAWINGS

FIG. 1 is a perspective view of a patient monitoring system embodying various features of the invention.

FIG. 2 is an enlarged, exploded view of a moisture trap for use in the system shown in FIG. 1.

FIG. 3 is an enlarged, cross-sectional view of the moisture trap shown in FIG. 2.

FIG. 4 is a cross-sectional view of the moisture trap shown in FIG. 3 taken along line 4—4.

FIG. 5 is a view of the moisture trap illustrated in FIG. 2 taken along line 5—5.

FIG. 6 is an enlarged view of a portion of the moisture trap shown in FIG. 3.

FIG. 7 is a partial, cross-sectional view of the moisture trap shown in FIG. 6 taken along Line 7—7.

Before one embodiment of the invention is explained in detail, it is to be understood that the invention is not limited in its application to the details of construction and the arrangements of components set forth in the following description or illustrated in the drawings. The invention is capable of other embodiments and of being practiced or carried out in various ways. Also, it is to be understood that the phraseology and terminology used herein is for the purpose of description and should not be regarded as limiting.

DETAILED DESCRIPTION

As illustrated in FIG. 1, a patient monitoring system 10 embodying this invention includes a device 12 for collecting a flow of a patient's exhalation. While the collection device 12 is shown in the form of a mask placed over a patient's nose and mouth, other standard collection devices can be used.

The monitoring system 10 also includes a sensing device 14. While it is understood that various sensing devices could be successfully and advantageously used, it is contemplated that in the preferred embodiment the sensing device 14 is a conventional infrared spectrometer operable to analyze the gaseous composition of the patient's exhalation including, for example, carbon dioxide or anesthesia gas content. It is also contemplated that the sensing device 14 include an apnea monitor (now shown) for detecting a complete stoppage of the flow of exhalation.

A pair of conduits 16, 18 communicate between the collection device 12 and the sensing device 14 to provide the flow path for the exhalation. Conduits 16, 18 can be standard conduits or cannulas. In the preferred embodiment, the conduits are made of a conventional flexible clear plastic.

A moisture trap 20 is connected between the conduits 16, 18 and between the collection device 12 and the sensing device 14. Trap 20 is provided to remove moisture from the flow of exhalation to protect the sensing device 14 from the introduction of moisture and insure the reliability of the sensor as a patient monitor.

The moisture trap 20 includes a generally cylindrical housing 22 having a longitudinal axis 24. A first end 26 has an aperture 28 and support means 30 for receiving conduit 16 (not shown in FIGS. 2 and 3). Support means 30 includes a male fitting 32 having a bore 34 aligned with aperture 28 and capable of releaseably receiving an end of conduit 16 (not shown). The conduit 16 will fit over fitting 32 and is held in position between that fitting and cylindrical body 31 by circumferential ribs 33 on the inner side of body 31. In the illustrated embodiment, the male fitting 32 is a standard male Luer-type fitting and is integrally formed with housing 22.

The housing 22 also includes an opposite or second end 36 having an aperture 38 and a generally annular rim 40 extending axially outwardly around the circumference of the second end 36 of the housing 22. With reference to FIG. 2, a first plurality of spoke-like members 42 extend inwardly from the rim 40. Relative to axis 24, these members extend radially and project axially outwardly from the second end 36. The second end 36 of housing 22 also supports a coupling 50. The coupling 50 is in the form of a female fitting 52 having a bore 48. In the illustrated embodiment, the female fitting 52 is of the female Luer-type and receives an end of conduit 18 (not shown) within bore 48 and through that conduit communicates with the sensing device 14. In an alternative embodiment of the invention, the coupling 50 can be in the form of a threaded nipple (not shown)

adapted to be screwed directly into the sensing device 14 and eliminate conduit 18. The coupling 50 also has a second end 54 received within the annular rim 40 and, as best shown in FIG. 5, a second plurality of spoke-like members 56 extending inwardly and radially similar to members 42. In the preferred embodiment, the coupling 50 and the second end 36 of the housing 22 are joined together by sonic welding the second end 54 of the coupling 50 to the rim 40 for a strong, gas tight joint. When assembled, the second end 36 of housing 22 and the end 54 of the coupling 50 define a cavity 58 therebetween. The first set of members 42 and the second set of members 56 extend into the cavity 58 and, for a purpose which will be more completely described below, are closely spaced but do not engage or intermesh.

The housing 22 also has an outer wall 60 which, with ends 26 and 36, define a chamber 62. Projections 64 and 65 extend inwardly from ends 26 and 36, respectively, and generally parallel to the outer wall 60. Projections 64 and 65 join within body 60, partitioning the chamber 62 into a central passageway 66 and a reservoir 68 surrounding the central passageway 66. The central passageway 66 extends along the axis 24 and between the first and second ends 26 and 36 for transferring the flow of exhalation through body 60 from one end to the other. As best shown in FIG. 3, the central passageway 66 communicates with aperture 28 in the first end 26 and with aperture 38 in the second end 36 and opens into the cavity 58 formed by the coupling 50 and the second end 36 of housing 22.

The inwardly extending projection 65 has a notch forming, with projection 64, a single opening 70 providing communication between the reservoir 68 and the central passageway 66. More particularly, and with reference to FIGS. 2 and 3, face 71 of projection 65 is spaced from but opposed to end 73 of projection 64. Both face 71 and end 73 are spaced inwardly from their respective axial ends, i.e., at ends 26 and 36, of the passageway 66 defined by projections 64 and 65. The remainder of the opening 70 is defined b peripheral edges 75 and 77 in the wall of projection 65. Edges 75 and 77 are spaced apart in opposed relation and extend between face 71 and end 73 in the final assembly illustrated in FIG. 3.

For ease of assembly, the housing 22 is made of plastic and is bisected by a plane 72 into a first half 74 and a second half 76 both halves are generally cup-shaped, i.e., U-shaped in cross-section, with the closed ends 26 and 36 extending generally perpendicular to the axis 24 and the outer walls extending generally parallel to the axis. Projections 64 and 65 meet at the plane 72 to form passage 66. The halves of the housing 22, when assembled, form a shear-type connection at 82 and are joined together, as for instance by sonic welding, for a strong, watertight joint.

At this point it should be noted that the end 26 with coupling 30, projection 65 and the outer walls is molded as a one-piece plastic structure. Similarly, end 36, coupling receiving rim 40, projection 64 and the outer walls are molded as a one-piece plastic structure.

The moisture trap 20 includes hydrophilic means within the body 60 for removing moisture from the flow of exhalation. In the preferred embodiment, the hydrophilic means includes an elongated, generally cylindrical column 86 made of porous, hydrophilic material and located in the central passageway 66. As best illustrated in FIG. 4, the hydrophilic column 86 only partially obstructs the central passageway 66 in that it has a cross-sectional area smaller than the cross-sectional area of the central passageway 66. This provides clearance allowing smooth, but restricted flow of exhalation along the inner wall of the central passageway 66. The shape column 86 is selected to have a surface area and volume sufficiently large to remove moisture from the exhalation as it flows along the inner wall of the passageway 66 and over and around column 86, and in some instances through the column. Various shapes can be used (square, rectangular, cross, elliptical) to provide as much surface area as possible consistent with the other needs of the device. The preferred shape as shown is cylindrical. The column should fill from 75-90% of the passage. In the preferred embodiment, the central passageway 66 has an internal diameter of approximately 0.170 inches and the hydrophilic column has a diameter of approximately 0.155 inches and a length of approximately 1.5 inches. The column filling approximately 75 to 90% of the passage, in the illustrated embodiment it fills 83% of the passage.

The hydrophilic material in the trap also includes a reservoir portion 88 made of hydrophilic material shaped to fit in and substantially fill the reservoir 68. In the illustrated embodiment, the hydrophilic reservoir portion 88 is divided into two halves for ease of assembly. A first half 90 which is shaped to fit in and generally fill the first half 74 of the housing 22 and a second half 92 shaped to fit in and generally fill the second half 76 of the housing 22. Both halves 90 and 92 are generally cylindrical.

The moisture trap 20 also includes means 94 made of hydrophilic material for wicking moisture to the hydrophilic reservoir portion 88 from the passage 66, specifically from hydrophilic column 86. This, to some extent, will remove moisture directly from the flow of exhalation and to a greater degree from the column 86 and transports it to the reservoir portions 90 and 92 for storage remote from the passageway for the stream of exhalation. The means 94 for wicking moisture to the reservoir takes the form of projection 96 on and a part of body 90 and projecting into the cylindrical opening 97 passing through reservoir portion 90. Wick projection 96 extends through the opening 70 and contacts the column 86. The wick 96 substantially fills the entire opening 70.

The hydrophilic wick 96 draws condensation collected by the column 86 away from the column 86, and thus away from the stream of subsequent exhalations, and through the opening 70 and to the hydrophilic reservoir portion 88. Because the housing 22 is sealed by the joint 82, moisture cannot escape from the hydrophilic reservoir portion 88 through the housing 22. Moisture distributes itself throughout the reservoir portions 90 and 92.

Hydrophilic material used in moisture traps such as those to which this invention relates is porous. As a result, it can absorb and hold gaseous media as well as moisture. The problem which results is the absorbed gaseous media can be released into subsequent exhalation streams from the hydrophilic material. In patient monitoring moisture traps, this means portions of the gases entrained in the patient's exhalation can be held in the hydrophilic material with the risk of such previously held gases being released into a subsequent stream, or streams, of exhalation. Such an occurrence results in readings of such subsequent exhalation streams which are not a reliable indication of current patient condition. The moisture trap of this invention is intended to provide adequate moisture separation while minimizing the exposure of exhalation stream to prior exhalation remnants.

To minimize contamination of exhalation, column 86 is sized and shaped to effectively remove moisture from a passing flow of exhalation with a minimum volume of hydrophilic material as compared to that of the media in which the separated moisture is stored.

This minimization of contamination is achieved in the preferred embodiment in that moisture drawn by the wick 96 through the opening 70 dampens the wick, it absorbs moisture and effectively seals the opening 70 to restrict passage of gaseous media from the central passageway into the reservoir 68. Similarly, any gaseous media already contained in reservoir 68 is also prevented from returning to the central passageway 66 for entrainment in exhalations by the seal provided by the dampened wick in the restricted opening 70.

The tubular inner wall defining passageway 66 isolates the reservoir portions 90 and 92 from direct flow of exhalation through the passageway. The only exposure of the exhalation stream to portions 90 and 92 is through opening 70 and wick 96. Opening 70 occupies only a limited amount of the circumferential periphery of the walls forming the passageway and extends only over a limited portion of the axial extension of the passageway. Since the volume of column 86 is relatively small as compared to the entire volume of reservoir portions 90 and 92, the probabilities of gaseous medium being entrapped in column 86 in any appreciable amount, which could contaminate later exhalation streams, are greatly reduced.

The percentage of the hydrophilic material actually exposed to the exhalation stream, the column 86, relative to total amount of hydrophilic material available for moisture removal and storage is approximately in the range of 0.3 to 0.6%. In the preferred illustrated embodiment, it is approximately 0.4%.

A suitable hydrophilic material for the hydrophilic column 86, wick 96 and reservoir portion 88 has a porosity of approximately 3 microns and is manufactured by Porex Technologies of Fairburn, Ga.

The moisture trap 20 also includes means 100 extending across the exit end of passsageway 66 for permitting passage of a flow of gas while repelling any moisture which might be entrained with the exhalation. This means is located downstream of the wick 96 and preferably downstream of column 86. In the illustrated embodiment, means 100 takes the form of a wafer-shaped filter 102 of hydrophobic material located in the cavity 58 at the second end 36 of the housing 22. The hydrophobic filter 102 prevents passage of water therethrough but allows gases such as exhalation, entrained carbon dioxide and anesthesia gases, to pass therethrough. A suitable material for the hydrophobic filter 102 has a porosity in the range of approximately 0.45 to 1.2 microns, preferably 8 microns and is manufactured by Gelman Sciences, Inc. of Ann Arbor, Mich.

The hydrophobic filter 102 has a diameter generally equal to the inner diameter 37 of cavity 58 and divides the cavity, as viewed in FIG. 3, into an air space 104 above the filter and an air space or reservoir 106, below the filter. In order to utilize as much of the effective area of the hydrophobic filter 102 as possible, and as best shown in FIG. 7, the hydrophobic filter 102 is located in the space between the first set of spoke-like members 42 and the second set of spoke-like members 56 so as to be spaced both from the end of the aperture 38 and from the inner end of the coupling 50. The reservoir 106 is sufficiently large to allow moisture blocked by the hydrophobic filter 102 to collect in that reservoir but it is sized to avoid distortion of the flow of the exhalation by the collected moisture.

The first and second spoke-like members 42, 56 space the hydrophobic filter 102 from their adjacent surfaces. Those members and that spacing minimizes the amount of structure actually in contact with the filter so that the amount of available filter to permit free flow of gaseous media is not substantially reduced.

In operation, exhalation from the patient leaves through conduit 16, enters the central passage 66, and passes along the inner walls of the central passageway 66, over and through the hydrophilic column 86. As the flow of exhalation leaves moisture on the hydrophilic column 86, the wick 96 draws moisture from the hydrophilic column 86, as well as directly from the exhalation stream, to the hydrophilic reservoir portion 88. Because the wick 94 substantially fills the entire opening 70, the wet wick 94 effectively seals the opening 70 to restrict passage of gaseous media between the reservoir 68 and the central passageway 66.

After an extended period of operation, the reservoir portion 88 becomes saturated and does not accept moisture from the wick 94. Because moisture is not drawn away from the column 86 when the reservoir is saturated, the column 86 becomes saturated and does not remove moisture from the flow of exhalation. Relatively humid exhalation passes over the saturated column 86 and wick 94 and flows along the passageway 66 to the hydrophobic filter 102, which repels water in the exhalation but allows gases, including carbon dioxide and anesthesia gases, to pass through the filter 102 to the sensing device 14. Water repelled by the hydrophobic filter 102 collects in the end reservoir 106 and cannot escape the end reservoir 106 through or around hydrophobic filter 102. As condensation collects in the end reservoir 106, the level of condensation in the end reservoir 106 rises. The flow of exhalation passing through the passageway 66 and the end reservoir 106 flows around the accumulated condensation in the end reservoir 106 and through the hydrophobic filter 102 until the condensation in reservoir 106 rises to a level which effectively occludes the filter 102. Once accumulated condensation occludes the filter 102, the flow sensor in the sensing device 14 signals medical personnel that the moisture trap 20 is full. The trap can then be removed and replaced by a fresh trap.

On occasion, the flow of exhalation can become excessively humid, which can result in a surge of condensation entering the moisture trap 20. The disclosed embodiment of the moisture trap 20 is well-suited to absorb a surge of condensation as it provides means to collect and remove large quantities of condensation from the passageway 66 to a reservoir 68 having a sufficient capacity to accept a relatively large amount of moisture. In addition, filter 102 prevents any part of the surge of moisture which cannot be picked up by wick 96 from passing through the moisture trap 20 and into the sensing device 14.

Various features of the invention are set forth in the following claims:

We claim:

1. In a patient monitoring system including a sensor and conduit means, and wherein said conduit means is operative to connect a patient to said sensor so that a patient's exhalation is transferred from said patient to the sensor, the combination in said conduit means of a moisture trap, said moisture trap comprising, in combination, a housing having a longitudinal axis, means connected to a first end of said housing defining a first aperture opening into the interior of said housing and including means for receiving a portion of said conduit means, means connected to a second end of said housing and spaced axially from said first end, said means connected to said second end defining a second aperture opening into said housing interior and including means for receiving a portion of said conduit means, means defining a wall extending parallel to said axis and dividing the interior of said housing into a reservoir on one side of said wall and a flow passage on the other side of said wall, said flow passage being closed to said reservoir except through a restricted opening in said wall, said flow passage in flow communication with said first and second apertures, hydrophilic means in said reservoir, and means in said restricted opening for collecting moisture from fluid flowing in said flow passage and transporting said fluid to said hydrophilic means.

2. The combination of claim 1
including hydrophilic means positioned in but not filling said flow passage, and
wherein said means in said restricted opening comprises hydrophilic means in contact with said hydrophilic means in said reservoir and in said flow passage.

3. The combination of claim 2 wherein said hydrophilic material substantially fills said restricted opening.

4. The combination of claim 3 wherein the amount of said hydrophilic column in said passage is in the range of 75 to 90% of the volume of said passage.

5. The combination of claim 4 wherein the amount of said hydrophilic material in said column is within the range of approximately 0.3 to 0.6% of the total hydrophilic material in said column and in said reservoir.

6. The combination of claim 1 including
hydrophobic means located at said second end of housing and extending across said second aperture so that flow from said flow passage must contact said hydrophobic means.

7. The combination of claim 6
including means at said second end defining a chamber extending generally perpendicular to said axis and positioned at said second aperture, and
wherein said hydrophobic means substantially fills said chamber.

8. A method of dehumidifying a patient's exhalation and for protecting a patient exhalation monitoring system from the entry of condensation, comprising the steps of
(a) passing the exhalation along a gas impermeable passageway by a sufficient surface of hydrophilic material to absorb moisture from the exhalation;
(b) wicking moisture away from the hydrophilic material through a restricted opening in said passageway restricting flow of gas to isolate said impermeable passageway from the wicked away moisture except through the restricted opening; and
(c) passing the exhalation through a hydrophobic material which repels water.

9. A moisture trap comprising, in combination,
a housing,
means defining a reservoir within said housing,
means defining a fluid flow passage through said reservoir and said housing and isolating said flow passage from said reservoir except through a restricted opening,
hydrophilic material in said reservoir, and
means in said restricted opening communicating with said flow passage and said hydrophilic material for collecting moisture entrained in fluid flowing in said passage and for transporting said moisture to said hydrophilic material.

10. The moisture trap of claim 1 wherein
said housing has a longitudinal axis and said fluid flow is along said axis,
said means defining said fluid flow passage includes elongated wall means extending generally parallel to said axis and partitioning the interior of said housing into said fluid flow passage and said reservoir and containing said restricted opening.

11. The moisture trap of claim 10 wherein
said restricted opening is defined by opposed faces spaced inwardly from the opposite, axial ends of said fluid flow passage and by relatively spaced and opposed peripheral portions in said wall means which peripheral portions extend generally axially between said opposed faces.

12. The moisture trap of claim 10
including hydrophilic means in said fluid flow passage for removing moisture from said fluid flow, and
wherein said means in said restricted opening for collecting moisture comprises hydrophilic wick means operative to wick moisture from said hydrophilic means in said fluid flow passage and said fluid flow to said hydrophobic material in said reservoir.

13. The moisture trap of claim 12 wherein said hydrophilic wick means contacts with hydrophilic means in said fluid flow passage.

14. The moisture trap of claim 13 wherein said wick substantially fills said restricted opening.

15. A moisture trap comprising, in combination,
a housing having a longitudinal axis,
means in said housing defining an elongated tubular wall extending generally along said axis and defining in the interior of said housing a fluid flow passage on one side of said tubular wall and a reservoir area on the opposite side of said wall,
a column of hydrophilic material positioned in but not filling said fluid flow passage,
a quantity of hydrophilic material located in said reservoir,
means defining a restricted opening in said tubular wall through which said reservoir and said fluid flow passage communicate, and
hydrophilic material located in said restricted opening and contacting both said column of hydrophilic material and the hydrophilic material in said reservoir.

16. The moisture trap of claim 15 wherein said hydrophilic material substantially fills said restricted opening.

17. The moisture trap of claim 16 wherein the amount of said hydrophilic column in said passage is in the range of 75 to 90% of the volume of said passage.

18. The moisture trap of claim 16 wherein the amount of said hydrophilic material in said column is within the range of approximately 0.3 to 0.6% of the total hydrophilic material in said column and in said reservoir.

19. The moisture trap of claim 17 wherein the amount of said hydrophilic material in said column is within the range of approximately 0.3 to 0.6% of the total hydrophilic material in said column and in said reservoir.

20. A moisture trap comprising, in combination, a housing, means defining a reservoir within said housing, means defining a fluid flow passage through said reservoir and said housing, hydrophilic means in said reservoir in communication with the flow through said flow passage for removing and collecting moisture entrained in fluid flowing in said passage, and hydrophobic means downstream of said hydrophilic means and extending across said fluid flow passage for preventing moisture from flowing out of said housing through said hydrophobic means and for occluding said flow passage when the moisture reaching said hydrophobic means reaches a predetermined amount.

21. The moisture trap of claim 19 wherein said means defining said fluid flow passage also isolates said flow passage from said reservoir except through a restricted opening, and including means in said restricted opening communicating with said flow passage and said hydrophilic material for collecting moisture entrained in fluid flowing in said passage and transporting said moisture to said hydrophilic material.

22. The moisture trap of claim 21 wherein said housing has a longitudinal axis and said fluid flow is along said axis, said means defining said fluid flow passage includes elongated wall means extending generally parallel to said axis and partioning the interior of said housing into said fluid flow passage and said reservoir and containing said restricted opening.

23. The moisture trap of claim 22 including hydrophilic means in said fluid flow passage for removing moisture from said fluid flow, and wherein said means in said restricted opening for collecting moisture comprises hydrophilic wick means operative to wick moisture from said hydrophilic means in said fluid flow passage and said fluid flow to said hydrophilic material in said reservoir.

24. The moisture trap of claim 23 wherein said hydrophilic wick means contacts said hydrophilic means in said fluid flow passage.

25. The moisture trap of claim 21 wherein said hydrophobic means comprises a generally disc-like member positioned downstream of said hydrophilic wick means and extends across the path of fluid flowing through said passage so that all fluid flow must contact said generally disc-like member.

26. The moisture trap of claim 25 wherein the amount of said hydrophilic column in said passage is in the range of 75 to 90% of the volume of said passage.

27. The moisture trap of claim 26 wherein the amount of said hydrophilic material in said column is within the range of approximately 0.3 to 0.6% of the total hydrophilic material in said column and in said reservoir.

* * * * *

UNITED STATES PATENT AND TRADEMARK OFFICE
CERTIFICATE OF CORRECTION

PATENT NO. : 5,131,387
DATED : July 21, 1992
INVENTOR(S) : Gerald H. French, et al.

It is certified that error appears in the above—identified patent and that said Letters Patent is hereby corrected as shown below:

Column 5, line 40, "b" should be --by--

Claim 10, column 10, line 13, "1" should be --9--.

Signed and Sealed this

Tenth Day of August, 1993

Attest:

MICHAEL K. KIRK

Attesting Officer

Acting Commissioner of Patents and Trademarks